(12) United States Patent
Gonzalez

(10) Patent No.: US 10,675,147 B2
(45) Date of Patent: Jun. 9, 2020

(54) ADDITIVE MANUFACTURING INSIDE THE HUMAN EYE

(71) Applicant: AMO Development, LLC, Santa Ana, CA (US)

(72) Inventor: Javier G. Gonzalez, Palo Alto, CA (US)

(73) Assignee: AMO Development, LLC, Santa Ana, CA (US)

(*) Notice: Subject to any disclaimer, the term of this patent is extended or adjusted under 35 U.S.C. 154(b) by 137 days.

(21) Appl. No.: 15/890,153

(22) Filed: Feb. 6, 2018

(65) Prior Publication Data

US 2018/0221141 A1 Aug. 9, 2018

Related U.S. Application Data

(60) Provisional application No. 62/455,445, filed on Feb. 6, 2017.

(51) Int. Cl.
*A61F 2/16* (2006.01)
*B29C 64/30* (2017.01)
(Continued)

(52) U.S. Cl.
CPC .......... *A61F 2/1662* (2013.01); *A61F 9/0017* (2013.01); *A61F 9/00812* (2013.01); *A61F 9/00814* (2013.01); *A61F 9/00825* (2013.01); *B29C 64/135* (2017.08); *B29C 64/153* (2017.08); *B29C 64/30* (2017.08); *B29D 11/00105* (2013.01); *B29D 11/00134* (2013.01); *B33Y 10/00* (2014.12); *B33Y 40/00* (2014.12); *B33Y 70/00* (2014.12); *B33Y 80/00* (2014.12);
(Continued)

(58) Field of Classification Search
None
See application file for complete search history.

(56) References Cited

U.S. PATENT DOCUMENTS 5,720,894 A 2/1998 Neev et al.
5,957,915 A 9/1999 Trost
(Continued)

OTHER PUBLICATIONS

International Search Report and Written Opinion for Application No. PCT/US2018/017110, dated May 23, 2018, 10 pages.

*Primary Examiner* — David H Willse
*Assistant Examiner* — Javier G Blanco
(74) *Attorney, Agent, or Firm* — Johnson & Johnson Surgical Vision, Inc.

(57) ABSTRACT

Additive manufacturing techniques are used to form an artificial intra-ocular lens (IOL) directly inside the human eye. Small openings are formed in the cornea and lens capsule of the eye, and the crystalline lens is broken up and removed through the openings; then, a material is injected into the lens capsule through the openings, and the focal spot of a pulse laser beam is scanned in a defined pattern in the lens capsule, to transform the material in the vicinity of the laser focal spot to form the IOL in a layer-by-layer manner. In one embodiment, stereolithography techniques are used where a pulse UV laser source is used to photosolidify a photopolymer resin. The liquefied resin is injected into the eye through the openings, after which only part of the resin, having the shape of the desired IOL, is selectively cured with the UV laser beam, via progressive layer formation.

3 Claims, 3 Drawing Sheets

(51) Int. Cl.
   *A61F 9/00* (2006.01)
   *B33Y 10/00* (2015.01)
   *B29C 64/153* (2017.01)
   *B33Y 70/00* (2020.01)
   *B29C 64/135* (2017.01)
   *B33Y 80/00* (2015.01)
   *B29D 11/00* (2006.01)
   *B33Y 40/00* (2020.01)
   *A61F 9/008* (2006.01)
   *B29K 33/00* (2006.01)
   *B29K 29/00* (2006.01)
   *B29L 11/00* (2006.01)
   *B29L 31/00* (2006.01)
   *A61B 17/00* (2006.01)

(52) U.S. Cl.
   CPC . *A61B 2017/00154* (2013.01); *A61F 9/00834* (2013.01); *A61F 2009/0087* (2013.01); *A61F 2009/00872* (2013.01); *A61F 2009/00887* (2013.01); *A61F 2009/00889* (2013.01); *A61F 2210/0085* (2013.01); *A61F 2240/001* (2013.01); *B29K 2029/04* (2013.01); *B29K 2033/12* (2013.01); *B29L 2011/0016* (2013.01); *B29L 2031/7532* (2013.01)

(56) References Cited

U.S. PATENT DOCUMENTS

| | | |
|---|---|---|
| 5,984,916 A | 11/1999 | Lai |
| 6,019,472 A | 2/2000 | Koester et al. |
| 6,454,761 B1 | 9/2002 | Freedman |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 2009/0247998 A1 | 10/2009 | Watanabe et al. |
| 2009/0250828 A1 | 10/2009 | Rosen et al. |
| 2009/0326651 A1* | 12/2009 | Spoor ............... A61F 2/16 623/6.11 |
| 2010/0082017 A1 | 4/2010 | Zickler et al. |
| 2011/0319873 A1 | 12/2011 | Raksi et al. |
| 2011/0319875 A1 | 12/2011 | Loesel et al. |
| 2014/0239524 A1* | 8/2014 | Sahler ............... A61F 2/16 264/1.37 |
| 2015/0290030 A1* | 10/2015 | Suckewer ........... A61F 2/1613 606/5 |
| 2016/0287332 A1* | 10/2016 | Griffits ............ A61B 18/20 |
| 2016/0346128 A1 | 12/2016 | Watanabe et al. |

\* cited by examiner

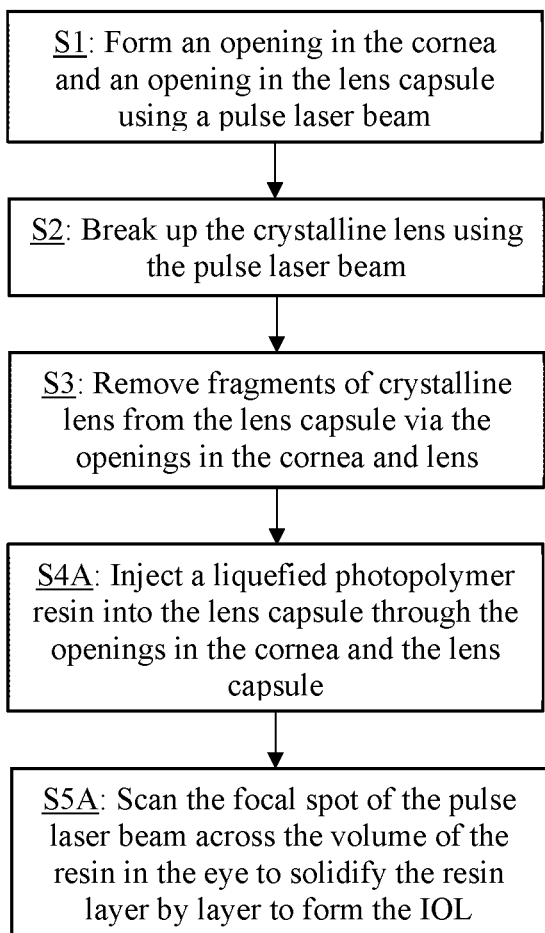
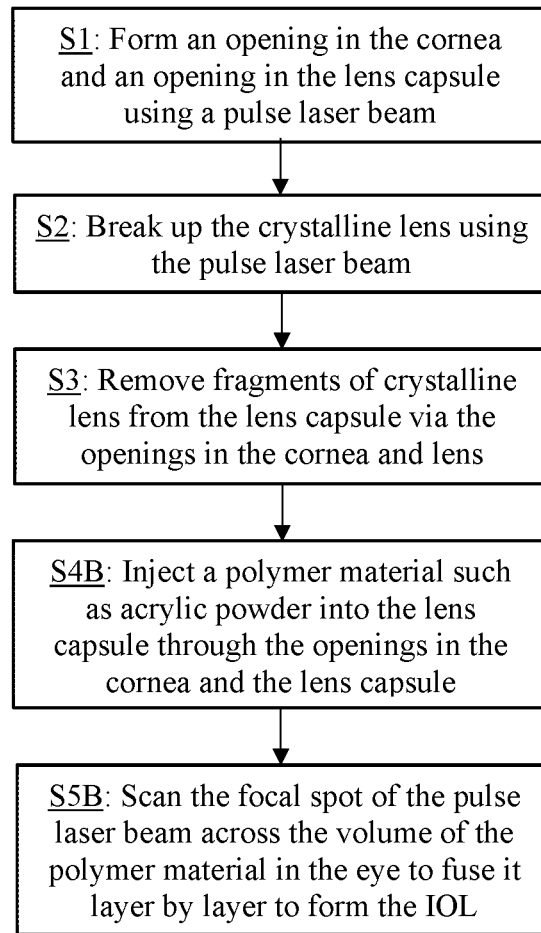
Fig. 2A
Fig. 2B

ADDITIVE MANUFACTURING INSIDE THE HUMAN EYE

CROSS-REFERENCES TO RELATED APPLICATIONS

This application claims the benefit under 35 U.S.C. § 119(e) of U.S. Provisional Patent Application No. 62/455,445, filed Feb. 6, 2017, which is incorporated herein by reference in its entirety.

BACKGROUND OF THE INVENTION

Field of the Invention

This invention relates to ophthalmic surgery, and in particular, it relates to an ophthalmic procedure that employs additive manufacturing inside the human eye.

Description of Related Art

Cataract treatment often consists of replacement of the opacified human crystalline lens by an artificial intra-ocular lens (IOL). The IOL is inserted into the patient's eye through an opening in the cornea. The incision size in the cornea depends on the IOL size. Although the incision in the cornea closes relatively fast due to the remarkable ability of the eye tissue to regenerate, it is hard to retain the optical characteristics of the cornea, and some residual diopters may be associated with the healing process of the cornea. The larger the incision, the larger the unknown optical aberrations induced. It is of interest to reduce the size of the incision into the cornea to minimize the severity of the optical aberrations.

Cataract surgery has improved significantly in the past few years with the advent of femtosecond laser surgery, where incisions to the cornea can be minimized to accommodate the insertion of the IOL and other surgical tools needed during the surgery. Opening into the outer layer of the human lens, also referred as capsule, are made nearly perfectly circular, with precise and reproducible diameter. Size and shape of the capsule opening, or capsulotomy, has a direct impact on the success and quality of the cataract surgery. Too big of a capsulotomy and the IOL is hard set in place while too small of a capsulotomy would render impossible the introduction of the IOL inside the capsule. Deviations from circularity in the capsulotomy often are related to distorted image forming on sight periphery. Femtosecond laser surgery produces perfectly circular capsulotomies and precisely sized corneal incisions with shaped cross section specially designed to expedite healing and reduce post-surgical visual aberrations. Nevertheless, the corneal incision produced by femtosecond laser surgery has to be barely but large enough to allow for the introduction of the IOL which is typically 2 mm wide. Manual surgery makes use of even bigger corneal incision, usually made with a surgical knife by the surgeon's hand. Manual incision does not have a cross section profile to expedite healing, so larger optical aberrations are expected.

More generally, laparoscopic surgery tries to minimize the recovery time by minimizing the incision size. Some surgical robots are available on the market for such procedures; for example, a surgical system is available that can perform prostate surgery with minor disruptions.

Also, a large array of implantable medical devices are available for treatment of numerous conditions, such as heart valves, insulin pumps and monitors, orthopedic screws, knew and hip replacements, etc. The same issue discussed above generally applies to any medical device that is implantable inside the human body, i.e., large devices require large incisions that take longer to heal.

SUMMARY

Embodiments of the present invention provide a method and system for building intra ocular lenses (IOLs) using additive manufacturing techniques ("3D printing") inside the eye.

This technique allows for manufacturing IOLs and other implantables inside the human body such as the eye via a tinny orifice just large enough to fit a manufacturing tool.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

In one aspect, the present invention provides a method of treating a patient's eye, which includes: using a pulse laser beam from a laser system to form an opening in a cornea and an opening in a lens capsule of the patient's eye; using the pulse laser beam from the laser system to break up a crystalline lens of the eye from the lens capsule; removing the broken up crystalline lens through the openings in the cornea and the lens capsule; injecting a material into the lens capsule through the openings in the cornea and the lens capsule; and forming an artificial IOL inside the lens capsule by scanning a focal spot of the pulse laser beam from the laser system inside the lens capsule in a defined scanning pattern to transform the material in a vicinity of the focal spot of the pulse laser beam.

In another aspect, the present invention provides a method for forming an artificial intra-ocular lens (IOL) inside a patient's eye, which includes: injecting a material into a lens capsule of the patient's eye, where a natural lens of the eye has been removed from the lens capsule; and forming an artificial IOL inside the lens capsule by scanning a focal spot of the pulse laser beam from the laser system inside the lens capsule in a defined scanning pattern to transform the material in a vicinity of the focal spot of the pulse laser beam.

In another aspect, the present invention provides a method for forming an artificial intra-ocular lens (IOL) inside a patient's eye, which includes: injecting a liquefied photopolymer resin into a lens capsule of the patient's eye to form a volume of the liquefied photopolymer resin in the eye, where a natural lens of the eye has been removed from the lens capsule; and forming the artificial IOL inside the lens capsule by scanning a focal spot of a pulse laser beam inside the volume of the resin in the eye, including: adjusting a depth of the focal spot of the pulse laser beam within the volume of the liquefied photopolymer resin; scanning the focal spot of the pulse laser beam in a lateral plane at the adjusted depth across a defined area, wherein the resin is solidified in a vicinity of the focal spot of the pulse laser beam; and repeating the adjusting step and the scanning step.

In another aspect, the present invention provides a method of treating a patient's eye, which includes: using a pulse laser beam from a laser system to form an opening in a cornea and an opening in a lens capsule of the patient's eye; using a pulse laser beam from the laser system to break up a crystalline lens of the eye from the lens capsule; removing the broken up crystalline lens through the openings in the cornea and the lens capsule; injecting a liquefied photopolymer resin into the lens capsule through the openings in the cornea and the lens capsule, to form a volume of the liquefied photopolymer resin in the eye; and forming an artificial IOL inside the lens capsule by scanning a focal spot of a pulse laser beam from the laser system inside the volume of the resin in the eye, including: adjusting a depth of the focal spot of the pulse laser beam within the volume of the liquefied photopolymer resin; scanning the focal spot of the pulse laser beam in a lateral plane at the adjusted depth across a defined area, wherein the resin is solidified in a vicinity of the focal spot of the pulse laser beam; and repeating the adjusting step and the scanning step.

It is to be understood that both the foregoing general description and the following detailed description are exemplary and explanatory and are intended to provide further explanation of the invention as claimed.

BRIEF DESCRIPTION OF THE DRAWINGS

FIGS. 2A-2D schematically illustrate methods for forming an artificial IOL using additive manufacturing inside the human eye according to embodiments of the present invention.

DETAILED DESCRIPTION OF PREFERRED EMBODIMENTS

Various techniques may be employed for intra-body-manufacturing, and in particular, for manufacturing IOLs inside the eye. Some of these techniques use a laser source to either etch the material into shape, or to selectively cure it into shape.

In a first embodiment, stereolithography techniques are used, where a pulse UV laser source is used to photosolidify a photopolymer resin. The liquefied resin is injected into the eye by a small opening in the eye, after which only part of the resin, having the shape of the desired IOL, is selectively cured with the UV laser beam, via progressive layer formation. The rest to the polymer is removed, or absorbed.

Figure 2C:
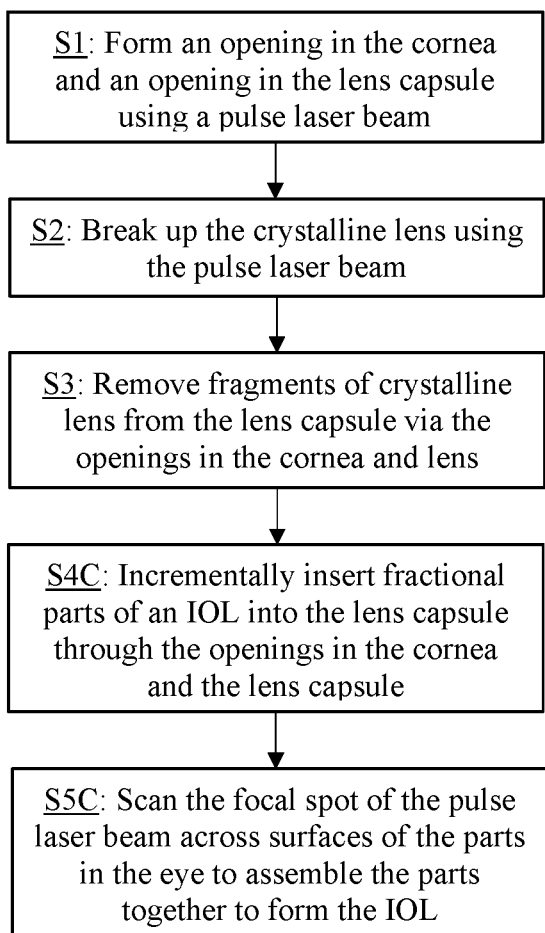

More specifically (see FIG. 2A), using a pulse laser surgery system, a single small opening is cut into the cornea and a capsulotomy of desired shape is cut into the surface of the human crystalline lens (lens capsule) (step S1). Subsequently, the human crystalline lens is broken up (phacofragmentation) using a laser beam, or using ultrasound energy by a phaco-emulsification tip (step S2), and the fragments are suctioned out (step S3). The same openings to the cornea and lens capsule are used to inject a drop of photopolymer resin into the lens capsule (step S4A). Then, a pulse laser beam is focused at a desired depth, and scanned in a lateral plane across a defined area within the volume of resin in the lens capsule (step S5A). Curing of the resin occurs in the vicinity of the focal spot of the laser beam where sufficient energy density is present. By scanning the focal spot across a defined area in a plane, a solidified resin layer having the defined shape is formed. After forming a layer, the focal spot depth of the laser beam is adjusted, and the beam is scanned at the new depth across another defined area, to form another solidified layer of resin on the surface of the previously formed layer. The scanning step is repeated to progressively solidify a part of the liquefied resin into the desired 3D shape of an IOL with the desired prescribed power and astigmatic correction.

Figure 1:
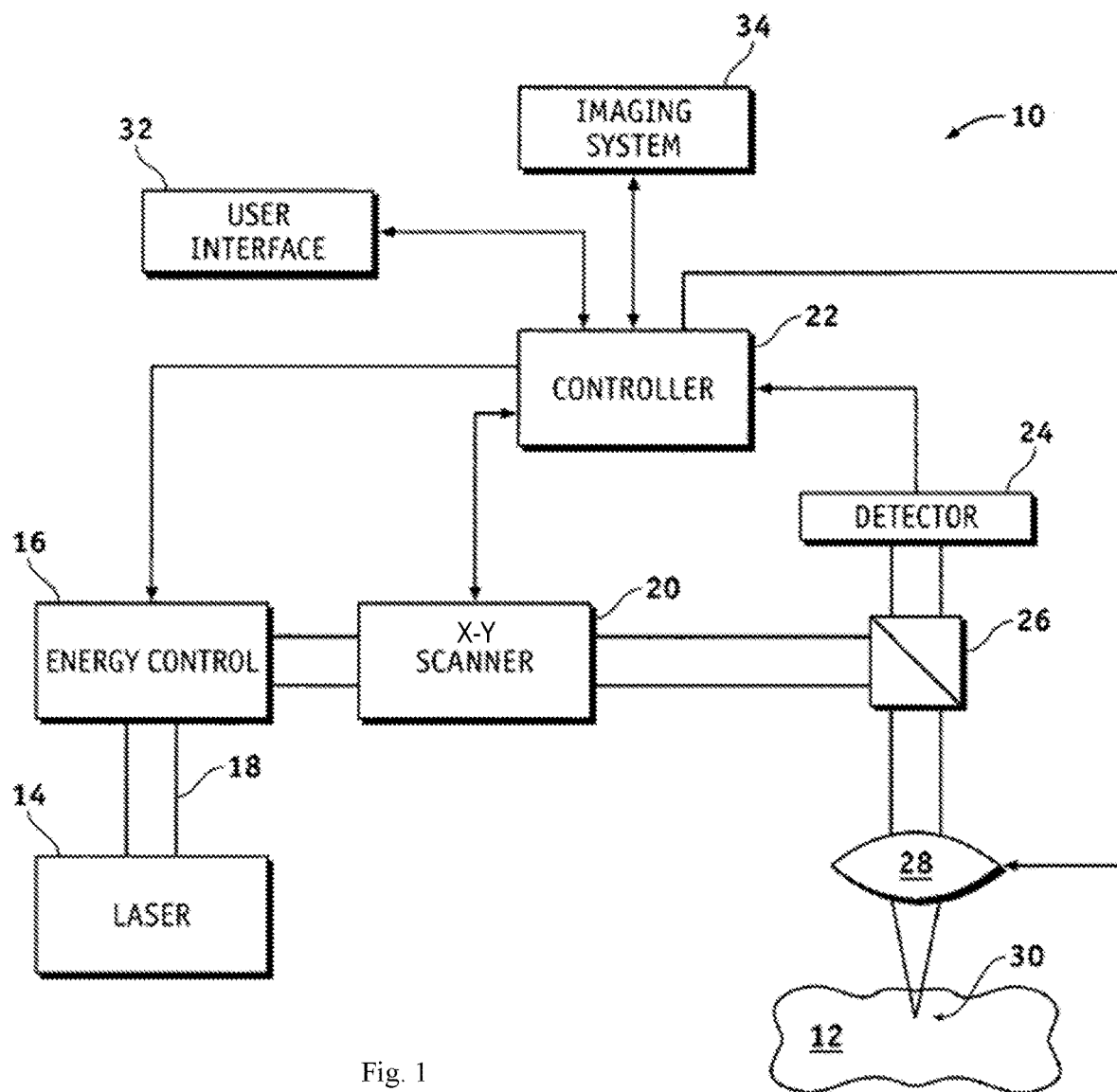
FIG. 1 illustrates a laser system that may be employed to implement embodiments of the present invention.

Various ophthalmic laser surgery systems are known and may be used to perform stereolithography in this embodiment. An ophthalmic laser surgery system uses a laser delivery system to deliver a laser beam generated by a laser into a patient's eye. The laser delivery system focuses the laser beam and scans the focal spot over an area or volume of the eye (referred to as the treatment area or region) to achieve desired therapeutic effects, such as photoalteration of the eye tissues. FIG. 1 is a block diagram that schematically illustrates an ophthalmic laser surgery system 10. The system 10 includes a laser 14 capable of generating a pulsed laser beam 18, an energy control module 16 for controlling and varying the pulse energy of the pulsed laser beam 18, a scanner 20 for scanning the laser beam, focusing optics 28 for directing the pulsed laser beam 18 on the surface of or within the region 12 (e.g., sub-surface) of the patient's eye, an imaging system 34 for displaying a real-time digital image of the patient's eye and providing other information, a controller 22, and a user interface 32 for the operator to interact with the system. The scanner 20 is controlled by the controller 22 to scan the focal spot of the laser beam within the eye. The controller 20 includes a processor and a memory device storing data and program code, including data and program code for controlling the scanner 20 to scan the laser beam according to defined scan patterns. The system 10 also includes a beam splitter 26 and a detector 24 coupled to the controller 22 to provide a feedback control mechanism for the pulsed laser beam 18. The laser 14 may be, for example, an ultrashort pulse laser, e.g. a femtosecond laser that can output a pulsed laser beam having a pulse width in the picosecond to femtosecond range. In some systems, some components, such as the beam splitter 26 and detector 24, may be omitted; some other systems may include additional components not shown in FIG. 1, such as a range finding system, etc.

In this embodiment, any suitable photopolymer resin may be used. Many known materials are suitable for this purpose. For example, U.S. Pat. Appl. Pub. No. 2009/0250828 describes a method for making ophthalmic devices using single mold stereolithography outside of the eye. This publication describes a number of photocurable materials that can be cured by UV light for purpose of making the ophthalmic devices, such as water-soluble crosslinkable poly(vinyl alcohol) prepolymer, more specifically, a polyhydroxyl compound.

The pulse laser used to photosolidify the resin may be the same pulse laser used to form the corneal incision, capsulotomy and phacofragmentation, or a different laser. The parameters (e.g. pulse energy, pulse duration, pulse repetition rate, wavelength) of the laser pulses suitable for this step may be determined based on the properties of the photopolymer resin used. The scan pattern of the laser focal spot for each layer is determined based on the properties of the photopolymer resin and the desired shape of the IOL to be formed. Note that the shape of the IOL is determined by the scan patterns for each layer, not by the shape of the liquefied resin inside the lens capsule.

To prevent the partially formed IOL from moving in the lens capsule during laser scanning, which would impact the accuracy of the shape of the formed IOL, a temporary anchor structure, such as two haptics, may be formed early in the photosolidification process. The anchor structure extends to the lens capsule to prevent movement of the partially formed IOL. The temporary anchor structure may be removed after the IOL is formed, or it may be kept as a part of the haptic of the finally formed IOL.

In a second embodiment (see FIG. 2B), referred to as selective layer sintering, a body of polymer is progressively formed inside the eye, in a layer-by-layer manner, by progressively fusing a polymer together (step S5B). A pulse UV laser is used to fuse the material into shape. This technique differs from the stereolithography technique (first embodiment) in that the polymer is not cured but melted by the laser beam and fused together. An example of a polymer that may be useful in this embodiment is acrylic powder which may be injected into the eye (step S4B). Other aspects of the second embodiment are similar to those of the first embodiment.

In a third embodiment (see FIG. 2C), referred to as laminated object manufacturing, fractional parts of an IOL, such as individual thin layers (slices) of an IOL, are introduced into the eye through the openings in the cornea and the lens capsule (step S4C). Once two parts are inserted inside the eye, they are assembled together (step S5C). Incremental insertion and assembling of additional IOL layer eventually lead to the complete assembly of the IOL. Compared to conventional technologies which insert a single monolithic IOL, only smaller parts are inserted using this technique; thus, comparatively small corneal openings are required. A material that may be useful in this embodiment is PMMA (polymethyl methacrylate), and the slices may be assembled by melting a surface thin layer of the material by scanning a pulsed laser beam across the surface (step 5C). Other aspects of the third embodiment are similar to those of the first embodiment.

Figure 2D:
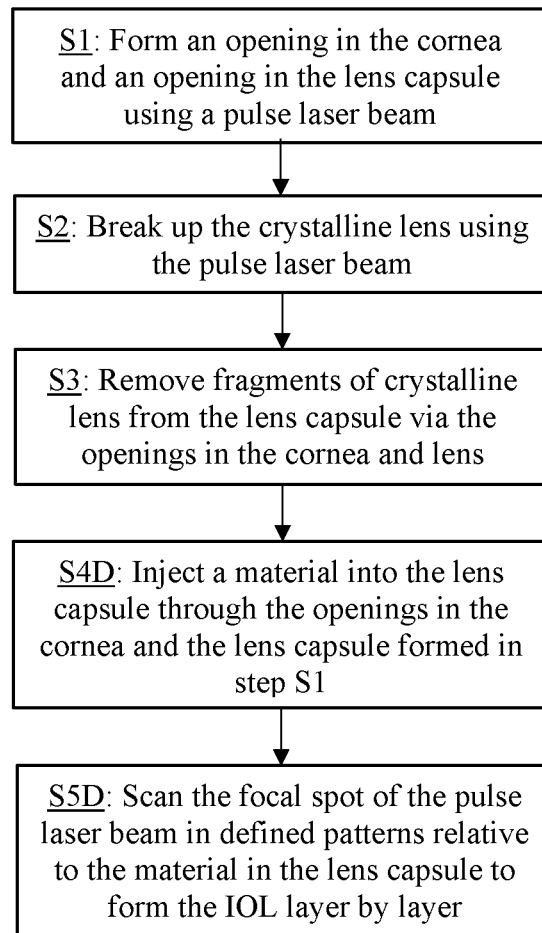

Stated more generally (see FIG. 2D), in the above embodiments, after forming openings in the cornea and lens capsule (step S1), breaking up the crystalline lens (step S2), and removing fragments of crystalline lens from the lens capsule through the openings (step S3), a material, such as a polymer, fractional parts of the IOL, etc., is injected into the lens capsule through the openings in the cornea and the lens capsule formed in step S1 (step S4D). Then, a pulse laser beam is focused at desired depths and the focal spot is scanned across defined areas relative to the material in the lens capsule (step S5D), such that the material is transformed either physically or chemically or both in a layer by layer manner to form an IOL. The scan pattern of the laser beam is controlled by the controller 20 which executes program code stored in its memory.

In a fourth embodiment, referred to as laser etching, an existing lens can be reshaped so as to adjust the correction after the original surgery. For example, if after surgery, the residual astigmatism is 1 diopter, then a pulse laser beam may be used to remove additional IOL materials in a manner that reshapes the IOL and modifies its optical properties. In this particular example the IOL prescriptive power is adjusted by 1 diopter.

Using these techniques, an IOL can be built inside the anterior chamber of the eye, through a minuscule hole, just large enough to introduce a manufacturing tip or individual smaller/thinner parts of the IOL. In some of the described techniques, the same laser used to perform preliminary steps of the procedure (such as capsulotomy) is used to interact with the material to form the IOL.

Using the same principles and techniques described above, other implantable devices such as stents, etc. may be manufactured inside the human body. The laser beam may be introduced to the manufacturing site by a catheter and/or an optical fiber.

It will be apparent to those skilled in the art that various modification and variations can be made in the method and apparatus for performing additive manufacturing inside the human eye according to the present invention without departing from the spirit or scope of the invention. Thus, it is intended that the present invention cover modifications and variations that come within the scope of the appended claims and their equivalents.

What is claimed is:

1. A method for forming an artificial intra-ocular lens (IOL) inside a patient's eye, comprising:

using a pulse laser beam from a laser system to form an opening in a cornea and an opening in a lens capsule of the patient's eye;

using the pulse laser beam from the laser system to break up a crystalline lens of the eye from the lens capsule;

removing the broken up crystalline lens through the openings in the cornea and the lens capsule;

injecting a liquefied photopolymer resin into the lens capsule through the openings in the cornea and the lens capsule, wherein the injected liquefied photopolymer resin forms a volume of the liquefied photopolymer resin inside the lens capsule; and forming said artificial IOL directly inside the lens capsule by scanning a focal spot of the pulse laser beam from the laser system inside the lens capsule in a defined scanning pattern to transform the liquefied photopolymer resin in a vicinity of the focal spot of the pulse laser beam;

wherein the liquefied photopolymer resin is photosolidified in the vicinity of the focal spot of the pulse laser beam;

wherein the forming step includes:

adjusting a depth of the focal spot of the pulse laser beam within the volume of the liquefied photopolymer resin;

scanning the focal spot of the pulse laser beam in a lateral plane at the adjusted depth across a defined area; and repeating the adjusting step and the scanning step such that the liquefied photopolymer resin is transformed in a layer by layer manner to form the IOL; and wherein the scanning pattern of the focal spot of the pulse laser beam for each layer is determined based on the properties of the photopolymer resin and the desired shape of the IOL to be formed.

2. The method of claim 1, wherein the liquefied photopolymer resin includes a water-soluble crosslinkable poly(vinyl alcohol) prepolymer, and wherein the pulse laser beam is a UV pulse laser beam.

3. The method of claim 1, further comprising, after the forming step:

removing untransformed polymer material from the lens capsule.

* * * * *